United States Patent
Garst

(10) Patent No.: US 6,294,563 B1
(45) Date of Patent: Sep. 25, 2001

(54) COMBINATIONS OF PROSTAGLANDINS AND BRIMONIDINE OR DERIVATIVES THEREOF

(75) Inventor: Michael E. Garst, Newport Beach, CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/440,379

(22) Filed: Nov. 15, 1999

Related U.S. Application Data

(63) Continuation-in-part of application No. 08/710,636, filed on Mar. 17, 1998, now abandoned, which is a continuation of application No. 08/330,050, filed on Oct. 27, 1994, now abandoned.

(51) Int. Cl.[7] ................. A61K 31/415; A61K 31/215; A61K 31/19
(52) U.S. Cl. .................. 514/392; 514/530; 514/573; 514/912; 514/913
(58) Field of Search ................... 514/530, 573, 514/912, 913, 393

(56) References Cited

U.S. PATENT DOCUMENTS

| | | |
|---|---|---|
| 3,755,426 | 8/1973 | Strike et al. . |
| 3,890,319 | 6/1975 | Danielewicz et al. . |
| 4,029,681 | 6/1977 | Smith . |
| 4,029,792 | 6/1977 | Danielewicz et al. . |
| 4,097,489 | 5/1978 | Bundy . |
| 4,288,616 | 9/1981 | Sih . |
| 4,291,175 | 9/1981 | Wissner et al. . |
| 4,321,405 | 3/1992 | Weiss . |
| 4,343,949 | 8/1982 | Bernardy et al. . |
| 4,576,962 | 3/1986 | Matthews . |
| 4,599,353 | 7/1986 | Bito . |
| 4,614,825 | 9/1986 | Snitman et al. . |
| 4,994,274 | 2/1991 | Chan et al. . |
| 5,021,416 | 6/1991 | Gluchowski . |
| 5,091,528 | 2/1992 | Gluchowski . |
| 5,093,329 | 3/1992 | Woodward . |
| 5,173,298 | 12/1992 | Meadows . |
| 5,292,517 | 3/1994 | Chang . |
| 5,856,329 | 1/1999 | Wheeler et al. . |

FOREIGN PATENT DOCUMENTS

| | | |
|---|---|---|
| 3923797 | 1/1991 | (DE) . |
| 289349 | 11/1988 | (EP) . |
| 299914 | 1/1989 | (EP) . |
| 364417 | 4/1990 | (EP) . |
| 366279 | 5/1990 | (EP) . |
| 399839 | 11/1990 | (EP) . |
| 544899 | 1/1993 | (EP) . |
| 85/02841 | 7/1985 | (WO) . |
| 91/14428 | 10/1991 | (WO) . |
| 94/08585 | 4/1994 | (WO) . |

OTHER PUBLICATIONS

Hurvitz et al, Drugs, 41(4), 514–532 (1991),"New Developments in the Drug Treatment of Glaucoma".

Bito et al, "The Ocular Effects of Eicosanoids and Other Autacoids: Historic Background and the Need for a Broader Perspective", *The Ocular Effects of Prostaglandins and Other Eicosanoids*, Alan R. Liss, Inc., New York: 1989, 1–13.

Searle, J.B., "Pharmacological Advances in the Treatment of Glaucoma", Drugs Aging, Sep. 1994, 5 (3) P 156–70, New Zealand.

Yavitz, "LASIK study shows brimonidine provides neuroprotective effect", Ocul Surg News 1999 Sep. 1; 17(17):28.

Yuksel et al, "The Short–Term Effect of Aging Brimonidine 0.2% to Timolol Treatment in Patients with Open–Angle Glaucoma", Ophthalmologica 1999; 213(4); 228–233.

Yoles et al, "α2–Adrenoreceptor Agonists are Neuroprotective in a Rat Model of Optic Nerve Degeneration", IOVS, Jan. 1999, vol. 40, No. 1, pp. 65–73.

*Primary Examiner*—Zohreh Fay
(74) *Attorney, Agent, or Firm*—Cynthia O'Donohue; Carlos Fisher; Robert Baran

(57) ABSTRACT

The invention concerns combinations of alpha adrenergic agents such as brimonidine and its derivatives as represented by formula (I) below formula (I)

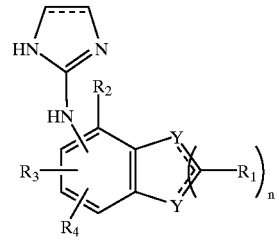

wherein each Y is independently selected from the group consisting of N, N—CH3, O, S and C—$R_1$; $R_1$ is hydrogen, lower alkyl or oxo; $R_2$, $R_3$ and $R_4$ are independently selected from the group consisting of hydrogen, halogen, lower alkyl and lower alkenyl; n is an integer from 1 to 3; and a broken line beside a solid line indicates either a single or a double bond with the proviso that when n=1, both bonds from Y to C—R1 cannot be double bonds, and prostaglandins known in the art to cause lowering of intraocular pressure which are useful in compositions, methods of treatment and articles of manufacture for the treatment of glaucoma and alleviation of elevated intraocular pressure and providing neuroprotection.

7 Claims, No Drawings

COMBINATIONS OF PROSTAGLANDINS AND BRIMONIDINE OR DERIVATIVES THEREOF

CROSS REFERENCE TO RELATED APPLICATIONS

This application is a continuation-in-part of application, Ser. No. 08/710,636, filed Mar. 17, 1998 as a Continued Prosecution Application of the application, Ser. No. 08/710,636, filed Sep. 18, 1996 now abandoned, which was a file wrapper continuation of application, Ser. No. 08/330,050, filed Oct. 27, 1994 now abandoned.

BACKGROUND OF THE INVENTION

1. Field of the Invention

The invention described herein relates generally to the field of glaucoma therapy. In particular the invention relates to the treatment of glaucoma and ocular hypertension by use of a combination of at least one compound chosen from brimonidine and its derivatives, and at least one prostaglandin or derivative.

2. Background of the Art

Glaucoma is an ocular disorder associated with elevated intraocular pressure (IOP) which is too high for normal ocular physiology and may result in irreversible loss of visual function. Owing to the progressive nature of glaucoma, the disease may begin with elevated IOP, progress through loss of visual field and eventually lead to blindness. Ocular hypertension, i.e., the condition of elevated intraocular pressure without optic nerve head damage or characteristic glaucomatous visual field defects, is now believed by many ophthalmologists to represent the earliest stage of glaucoma.

Many of the drugs formerly used to treat glaucoma proved not entirely satisfactory. Indeed, for a long period of time few advances were made in the treatment of glaucoma since pilocarpine and physostigmine were introduced. Only relatively recently have clinicians noted that many β-adrenergic blocking agents are effective in reducing intraocular pressure, however, they also have other characteristics, e.g. membrane stabilizing activity, that are not acceptable for chronic ocular use. (S)-1-tert-Butylamino-3-[(4-morpholino-1,2,5-thiadiazol-3-yl)oxy]-2-propanol (also known as timolol), a β-adrenergic blocking agent, was found to reduce intraocular pressure and to be devoid of many unwanted side effects associated with pilocarpine and, in addition, to possess advantages over many other β-adrenergic blocking agents, e.g., to be devoid of local anesthetic properties, to have a long duration of activity, and to display minimal tolerance. A decrease in aqueous formation by the ciliary processes is thought to be the mechanism of action of beta-adrenoceptor antagonists, but the physiological basis for this action has not been clearly demonstrated. A newer beta-blocker, betaxolol, has relatively selective $\beta_1$ blocking activity.

Standard treatment modalities include parasympathomimetic agents such as pilocarpine, carbachol, and phosphocholine iodide, which lower intraocular pressure (IOP) by increasing aqueous outflow through the trabecular meshwork. A newer form of pilocarpine as a gel produces a longer action. Adrenergic agonist medications, such as epinephrine (adrenaline) and its pro drug, dipivefrine (dipivalyl epinephrine), function by increasing uveoscleral outflow and trabecular outflow facility.

Certain members of the class of compounds known as $alpha_2$ adrenergics have also been found useful in the treatment of glaucoma. Members of this class of compounds include clonidine and apraclonidine (aplonidine, ALO 2145), which has been released for clinical use. Apraclonidine hydrochloride is a derivative of clonidine hydrochloride, an $alpha_2$ adrenergic agonist. Clonidine has previously been shown to lower IOP significantly, but has the potential to produce marked lowering of both systolic and diastolic blood pressures. Its major ocular effect appears to be a decrease in aqueous production. The structural modification to apraclonidine decreases corneal absorption and the drug's ability to cross the blood-brain barrier, minimizing the risk of centrally mediated cardiovascular side effects. Apraclonidine may also influence secondary avenues of aqueous outflow, such as uveoscleral outflow, and may also affect conjunctival and episcleral vascular flow. Another $\alpha_2$ receptor agonist currently in clinical trials for use in treating glaucoma and elevated IOP is brimonidine (UK 14304-18). Disclosures of this family of compounds and methods of using same are made in (a) U.S. Pat. No. 3,890,319, (b) U.S. Pat. No. 4,029,792 and (c) U.S. Pat. No. 5,856,329, the entire contents of which are incorporated herein by reference.

Another class of agents, referred to as carbonic anhydrase inhibitors, block or impede aqueous inflow into the anterior chamber by inhibiting the enzyme carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such gross disruption of a basic enzyme system is justified only during an acute attack of alarmingly elevated intraocular pressure, or when no other agent is effective. Almost 50% of patients taking these medications are unable to tolerate them because of their adverse effects, and there is thus much interest in the development of a topical carbonic anhydrase inhibitor with the potential for fewer adverse effects. MK 507 is the most recent and most potent compound in the series of topically active carbonic anhydrase inhibitors. It produces a mean decrease in IOP of 25% for as long as 12 hours. Adverse effects include blanching of the conjunctiva, minimal mydriasis and eyelid retraction. This drug has been approved in the US for use in prevention of elevated IOP after argon laser trabeculoplasty and iridotomy, and has potential uses in preventing an IOP rise after YAG laser posterior capsulotomy and cataract surgery in patients already on other anti-glaucoma medications. For a recent review of therapeutics in the treatment of glaucoma see Hurvitz L. M.; Kaufman P. L.; Robin A. L.; Weinreb R. N.; Crawford K. and Shaw B., *Drugs*. 41 (4), p. 514–32 (1991).

The topical use of prostaglandins in treating elevated IOP and glaucoma has been found to be effective in primates and in some clinical studies to a greater extent than most currently used therapeutic agents by topical administration to the eye. U.S. Pat. No. 4,599,353 to Bito describes the use of prostaglandins preferably $PGE_2$ and $PGF_{2\alpha}$ for topical treatment of glaucoma. U.S. Pat. No. 4,994,274 to Chan, et al. describes certain 11, 15-diacyl derivatives of prostaglandins for use in lowering IOP. European Published Application No. 544899 describes 13,14-di:hydro-15(R)-17-phenyl 18,19,20-trinor $PGF_{2\alpha}$ esters which are useful in treating elevated IOP. In contrast to the miotics, prostaglandins are believed to lower IOP by increasing the outflow of aqueous humor via the uveoscleral route. In addition, prostaglandins may possibly have other effects in the eye, such as enhancing vascular support of ocular tissues; however, there is no understanding of that mechanism at this time.

All six types of therapeutic agents have potentially serious side effects: miotics such as pilocarpine can cause blurring of vision and other visual side effects which may lead either to decreased patient compliance with the dosing regimen or to termination of therapy; carbonic anhydrase inhibitors can also cause serious side effects which affect patient compliance and/or necessitate the withdrawal of treatment; at least one beta-blocker, timolol, has increasingly become associated with serious pulmonary side effects attributable to its effect on $\beta_2$ receptors in pulmonary tissue; and prostaglandins often produce hyperemia and edema of the conjunctiva, resulting in redness and hyperesthesia of the eye, which may affect patient compliance. In addition to these side effects, a therapy regimen which includes the use of two or more pharmaceutical compositions containing drugs selected from two or more of the above-cited classes requires the patient to apply the compositions to the affected eye(s) in separate, spaced dosages, several times per day. Patient compliance with such complicated dosage regimens can be very poor, particularly in elderly patients. Since the majority of glaucoma patients are elderly, problems with patient compliance are significant considerations to the prescribing physician.

In light of the foregoing circumstances, it is clear that a need exists for new, more potent anti-glaucoma compositions which avoid or reduce the above-cited side effects, while increasing patient compliance. The present invention is directed to such uses and compositions.

SUMMARY OF THE INVENTION

It has unexpectedly been found that administration of one or more prostaglandins in combination with one or more brimonidine derivatives as defined below controls or lowers intraocular pressure (IOP) without the accompanying inflammatory response (including hyperemia) typically found with topical use of prostaglandins. Additionally it has unexpectedly been found that brimonidine derivatives exert a neuroprotective effect on the eye reducing the potential degeneration of nerves; for example, the optic nerve. The present invention therefore provides compositions, methods and articles of manufacture useful for the treatment of glaucoma and ocular hypertension which have the additional surprising effect of providing neuroprotection to the optic nerve. Thus, the present compositions have a combined effect of alleviating symptoms of glaucoma (reducing, intraocular pressure) as well as helping prevent progression of optic nerve degeneration. The compositions contain a combination of at least one brimonidine derivative and at least one prostaglandin which is effective in reducing or controlling IOP, and which has a reduction or elimination of the side effects normally associated with topical application of prostaglandins.

In a preferred formulatory embodiment of the compositions of the present invention, the above combinations may further include liquid formulations that contain resins which gel as a result of the increase of pH and/or temperature of the solution on administration to the eye, or polymeric drug vehicles that are suspended in perfluorocarbon or fluorinated silicone carriers which can advantageously be used in administration of non-preserved doses of the present drug combinations with enhanced bioavailability. U.S. Pat. No. 5 173 298 and 5 292 517 respectively disclose these improved ocular delivery systems and are herein incorporated by reference in their entirety.

U.S. Pat. No. 5 292 517 (Chang) discloses a sustained release pharmaceutical composition with long-term storage stability and comprises: porous ion exchange resin particles of 1–50 micron diameter incorporated in an aqueous solution of at least one reversibly gelling polymer selected from pH-sensitive and temp.-sensitive gelling polymers. The aqueous solution has a free flowing, drop instillable viscosity at room temperature and pH 2.5–4.0, and a gel-like viscosity at about 35° C. and pH 7.4. The pharmaceutical compounds are ionically bound within the pores of the ion exchange resin particles. The pores are sufficiently small to prevent the polymer from diffusing into the pores. Preferably the pH-sensitive gelling polymers are polyacrylic acids, polymethacrylic acids, polycrotonic acids, carboxypolymethylene and poly(methylvinylether/maleic acids). Preferably the thermally-sensitive gelling polymers are alkylcelluloses and hydroxyalkyl celluloses. The ion exchange resin particles preferably have exchange functionalities selected from sulfonic and carboxylic acids. The pharmaceutical combination remains bound within the pores of the ion exchange resin particles until after administration to the target tissue where small ions migrate into the pores and initiate ion exchange. The bioadhesiveness of the composition makes it useful for delivering ophthalmic pharmaceuticals to the surface of the eye, since it resists lachrymal drainage without interfering with vision.

U.S. Pat. No. 5 173 298 (Meadows) discloses non-aqueous compositions which comprise (a) a non-aqueous fluorinated liquid carrier, which is a perfluorocarbon or a fluorinated silicone; and (b) polymeric drug delivery vehicle (s), associated with therapeutic or diagnostic compounds, suspended in the fluorinated solvent. The perfluorocarbons may preferably contain N or O in the structure. A preferred embodiment of the polymeric carrier is poly (methylvinylether/maleic anhydride) copolymer. The composition has improved shelf life due to the absence of water to cause hydrolytic changes in the active agent or polymer, and the agent does not leach out into the carrier, and such stability allows multi-dose packaging. At the target site, drug is released at the preferred rate, e.g., from microparticulates or microcapsules to control administration. The composition is transparent and non-irritant. Low administration volumes make the composition especially suitable for ophthalmic purposes, allowing efficient delivery into the tear film without overflow that is blinked away and lost, or vision blurring as with, for example, oils. The volume to be delivered may be less than 10 $\mu l$ in comparison to the 35 $\mu l$ minimum of prior art water and oil based systems, and to the 7 $\mu l$ accommodation volume of the tear film.

DETAILED DESCRIPTION OF THE INVENTION

The present invention utilizes combinations of at least one brimonidine derivative and at least one prostaglandin to treat glaucoma and ocular hypertension and to provide neuroprotection.

Brimonidine is a known adrenergic compound, and is described for example in U.S. Pat. No. 3,890,319; the contents of this patent relating to the structure, preparation, and physical properties of this compound are incorporated herein by reference. It is also known that brimonidine and certain derivatives thereof are effective in lowering intraocular pressure when applied topically to the eye; this discovery is described in U.S. Pat. No. 5,021,416 (Gluchowski), the entire contents of which are incorporated herein by reference. A method of treating ocular neural injury with brimonidine and certain derivatives is described in U.S. Pat. No. 5,856,329 (Wheeler). Brimonidine and certain derivatives thereof have also exhibited neuroprotective effects in the eye; this discovery is reported in Yoles E.; Wheeler L. A.; and Schwartz M., *Invest. Ophthalmol. Vis. Sci.,* 40 (1), p.

65–73 (1999). The beta-blocker, timolol, also used for IOP lowering, did not exhibit neuroprotection. Brimonidine when administered adjunctively to patients on timolol gave a statistically significant IOP-lowering effect of about 20%. This use of brimonidine as adjunctive agent to increase the IOP lowering effect of a beta blocker is described in Yuksel N.; Altintas O.; Karabas L.; Alp B.; and Caglar Y., *Ophthalmologica.* 213(4), p. 213–233 (1999).

Additionally in medical applications other than glaucoma, brimonidine has reduced or prevented neurodegeneration. Nerve fiber thinning caused by the rise in pressure with use of the microkeratomes in laser in situ keratomileusis surgery (LASIK), was lessened or totally prevented by brimonidine. This report by Yavitz E., *Ocul. Surg. News,* 17 (17) p. 28 (Sep. 1, 1999) provides further evidence of the neuroprotection offered by brimonidine.

The brimonidine derivatives described in this patent are those represented by formula (I) below

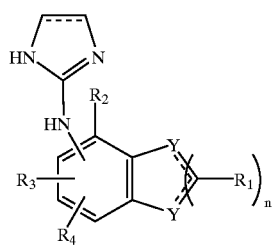

formula (I)

wherein each Y is independently selected from the group consisting of N, N—CH3, O, S and C—$R_1$; $R_1$ is hydrogen, lower alkyl or oxo; $R_2$, $R_3$ and $R_4$ are independently selected from the group consisting of hydrogen, halogen, lower alkyl and lower alkenyl; n is an integer from 1 to 3; and a broken line beside a solid line indicates either a single or a double bond with the proviso that when n=1, both bonds from Y to C-R1 cannot be double bonds.

U.S. Pat. No. 5 091 528 (Gluchowski) discloses other brimonidine derivatives which are encompassed by formula (I), namely benzoxazine ring derivatives which are useful in lowering IOP.

The terms "prostaglandin" and "PG" are generally used to describe a class of compounds which are analogs and derivatives of prostanoic acid (II)

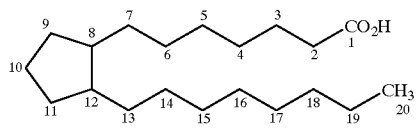

II

PG's may be further classified according to their 5-membered ring structure, using a letter designation. Ring structures given a letter designation are:

Prostaglandins of the A series (PGA's): 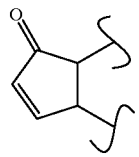

Prostaglandins of the B series (PGB's): 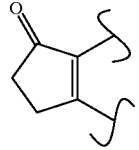

Prostaglandins of the C series (PGC's): 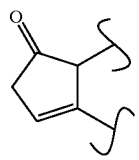

Prostaglandins of the D series (PGD's): 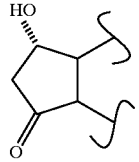

Prostaglandins of the E series (PGE's): 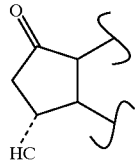

Prostaglandins of the F series (PGF's): 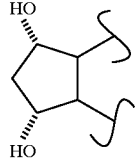

Prostaglandins of the J series (PGJ's): 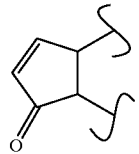

PG's may be further classified based on the number of unsaturated bonds on the side chain:

$PG_1$'s (13,14-unsaturated):

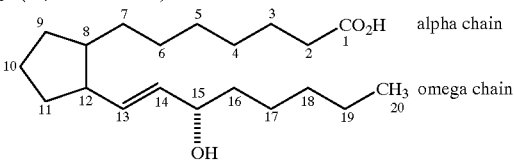

-continued

PG₂'s (13,14- and 5,6-unsaturated):

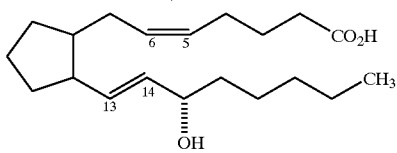

PG₃'s (13,14- and 5,6-and 17,18-unsaturated):

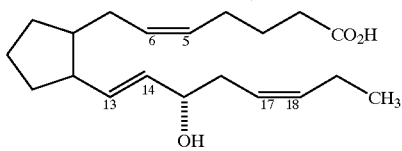

Other descriptors used in prostaglandin nomenclature are α: and β; these letters appended to the number of double bonds describe the stereochemistry of the attachments to the 5 membered ring.

An historical review of the ocular effects of prostaglandins and other eicosanoids can be found in Bito, L. and Stjernschantz, J., *The Ocular Effect of Prostaglandins and Other Eicosanoids*, Alan R. Liss, Inc., New York: 1989, 1–13.

The prostaglandins which may be utilized in the present invention include all pharmaceutically acceptable prostaglandins, their derivatives and analogs, and their pharmaceutically acceptable esters and salts (hereinafter collectively referred to as "prostaglandins" or "PG's"), which are capable of reducing intraocular pressure when applied topically to the eye. Such prostaglandins include the natural compounds: $PGE_1$, $PGE_2$, $PGE_3$, $PGD_2$, $PGF_{1\alpha}$, $PGF_{2\alpha}$, $PGF_{3\alpha}$, $PGI_2$ (prostacyclin), as well as analogs and derivatives of these compounds which have similar biological activities of either greater or lesser potencies. Analogs of the natural prostaglandins include but are not limited to: alkyl substitutions (e.g., 15-methyl or 16,16-dimethyl), which confer enhanced or sustained potency by reducing biological metabolism or alter selectivity of action; saturation (e.g. 13,14-dihydro) or unsaturation (e.g., 2,3-didehydro, 13,14-didehydro), which confer sustained potency by reducing biological metabolism or alter selectivity of action; deletions or replacements (e.g. 11-deoxy, 9-deoxo-9-methylene), which enhance chemical stability and/or selectivity of action; and omega chain modifications (e.g., 18,19,20-trinor-17-phenyl, or 17,18,19,20-tetranor-16-phenoxy), which enhance selectivity of action and reduced biological metabolism. Derivatives of these prostaglandins include all pharmaceutically acceptable salts and esters, which may be attached to the 1-carboxyl group or any of the hydroxyl groups of the prostaglandin by use of the corresponding alcohol or organic acid reagent, as appropriate. It should be understood that the terms "analogs" and "derivatives" include compounds which exhibit functional and physical responses similar to those of prostaglandins per se.

The following publications disclose examples of prostaglandins which are suitable for use in the present invention: Crabbe, P. (ed.), *Prostaglandin Research*, Academic Press, New York: 1977; Advances in Prostaglandin, Thromboxane, and Leukotriene Research, 14: 263–307 (1985); ibid. 14: 309–425; U.S. Pat. No. 3,884,969 (Schaub et al.); U.S. Pat. No. 3,873,607 (Bernady et al.); GB 1,444,971 (Floyd, Jr. et al.); U.S. Pat. No. 4,110,368 (Floyd, Jr. et al.); U.S. Pat. No. 4,291,175 (Wissner et al.); U.S. Pat. No. 4,321,405 (Weiss); U.S. Pat. No. 4,343,949 (Bernady et al.); U.S. Pat. No. 4,614,825 (Snitman et al.); U.S. Pat. No. 4,029,681 (Smith); U.S. Pat. No. 4,097,489 (Bundy); U.S. Pat. No. 4,288,616 (Sih): U.S. Pat. No. 3,755,426 (Strike et al.); U.S. Pat. No. 4,576,962 (Matthews); U.S. Pat. No. 4,599,353 (Bito); EP 364, 417 (Stjernschantz et al.); DE 3,923,797 (Klar et al.); WO 85/02841 (Skuballa et al.); EP 299,914 (Buchmann et al.); EP 399,839 (Woodward et al.); U.S. Pat. No. 4,994,274 (Chan et al.); WO 91/14428(Woodward); U.S. Pat. No. 5.093,329 (Woodward); EP 289,349 (Ueno et al.) and EP 366,279 (Ueno et al.). All of these publications are incorporated by reference herein with respect to their disclosures and teachings concerning prostaglandin structure, synthesis and activity. It is to be understood that prostaglandins disclosed in and taught by the above-referenced publications are only exemplary in nature; the present invention is not intended to be limited by the disclosures and teachings of the above-referenced publications.

Specific examples of prostaglandins which are useful in the present invention include: $PGF_{2\alpha}$, PGE2, PGE1, prostacyclin, 15(S)-methyl-$PGF_{2\alpha}$, 16,16-dimethyl-$PGF_{2\alpha}$, 15(S)-methyl-$PGE_2$, 16,16-dimethyl-$PGE_2$, 17,18,19,20-tetranor-16-phenoxy-PGE2, 17, 18, 19, 20-tetranor-16-phenoxy-$PGF_{2\alpha}$, 18, 19 ,20-trinor-17-phenyl-$PGE_2$, 18, 19, 20-trinor-17-phenyl-$PGF_{2\alpha}$, trimoprostil, RS-84–135, rioprostil, S-1033 (15-deshydroxy $PGF_{2\alpha}$, sodium salt), S-747260, nocloprost, CS-412, YPG-209, K-10134, cloprostenol, fluprostenol, luporstiol, etiproston, tiaprost, SQ 27986, ZK 138519, 13,14-dihydro-ZK 138519, ZK 118182, 13,14-dihydro-ZK 118182, ZK 110841, 13,14-dihydro-ZK 110841, PhXA41 (latanoprost), RO-221327, HR-466, HR-601, ONO-1206, UFO-21, 11-deoxy-$PGE_2$, 11-deoxy-$PGF_{2\alpha}$, 11-deoxy-16,16-dimethyl-$PGE_2$, 11-deoxy-15(S)-methyl-$PGE_2$, 11-deoxy-15(S)-methyl-$PGF_{2\alpha}$, misoprostol, enisoprost, MDL-646, CL-115,574, CL-115,347, TR-4161, TR-4752, TR-4367, CP-27987, sulprostone, gemeprost, alfaprostol, delprostenate, prostalene, fenprostalene, CL-116,069, ONO-995, RO-229648, as well as their pharmaceutically acceptable esters and salts, as appropriate for the respective individual structures. The most preferred prostaglandins are: $PGF_{2\alpha}$-11-pivalyl ester, the 1-amido-15-methyl ether of $PGF_{2\alpha}$, 1-ethylamido-18,19,20-trinor-17-phenyl-$PGF_{2\alpha}$, the free acid and lower alkyl ester derivatives of $PGF_{2\alpha}$ wherein the omega chain has been replaced with phenylethylsulfonamidomethyl- as represented by the structure below,

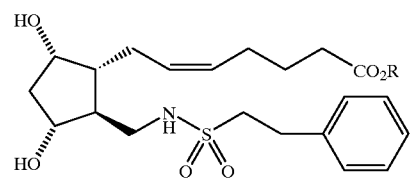

R = H, Me, Et, n-Pr, iPr, etc $PGF_{2\alpha}$-1-ethyl ester, $PGF_2$(x1-isopropyl ester, RO-229648, SQ 27986, ZK 38519, 13,14-dihydro-ZK 138519, ZK 110841, 13,14-dihydro-ZK 110841, PhXA41, and 18,19,20-trinor-17-phenyl-$PGF_{2\alpha}$-1-methyl ester. All of the foregoing compounds are known.

In general, compositions of the present invention will include one or more brimonidine derivatives in an amount between about 0.02 and about 2.0 percent by weight (wt %) and one or more prostaglandins an amount between about 0.00001 and about 0.2 wt %. It is preferred to use one or more brimonidine derivatives in an amount between about 0.05 and about 1.0 wt %, and it is especially preferred to use an amount between about 0.1 and about 0.25 wt %. It is preferred to use one or more prostaglandins in an amount between about 0.0001 and about 0.01 wt %, depending on the potency of the prostaglandin. The ratio by weight of brimonidine derivative to prostaglandin is generally between about 1:1 to about 10,000:1 and preferably between about 5:1 to about 1000:1. It should be understood that the ratio by weight of brimonidine derivative to prostaglandin will greatly depend on the potency of the prostaglandin used, since the potency of different prostaglandins may differ by as much as a factor of $10^5$.

In addition to the above-described principal active ingredients, the anti-glaucoma compositions of the present invention may further comprise various formulatory ingredients, such as anti-microbial preservatives and tonicity agents. Examples of suitable anti-microbial preservatives include: benzalkonium chloride, thimerosal, chlorobutanol, methyl paraben, propyl paraben, phenylethyl alcohol, edetate disodium, sorbic acid, Polyquad®, Dymed®, and other agents equally well known to those skilled in the art. Such preservatives, if utilized, will typically be employed in an amount between about 0.001 and about 1.0 wt %. Examples of suitable agents which may be utilized to adjust the tonicity or osmolality of the formulations include sodium chloride, potassium chloride, mannitol, dextrose, glycerin and propylene glycol. Such agents, if utilized, will be employed in an amount between about 0.1 and about 10.0 wt %.

The compositions of the present invention may additionally include components to provide sustained release and comfort. Such components include: porous ion exchange resin particles in aqueous solutions of reversibly gelling polymers with the therapeutic agent(s) bound in the resin pores; or drop instilled, low dose volume compositions for high bioavailability which have non aqueous perfluorocarbon or fluorinated silicone liquid carriers and a polymeric drug delivery vehicle.

In a preferred embodiment of the compositions of the present invention, the above combinations may further include non-aqueous, fluorinated drug delivery vehicles, pH sensitive, reversible gelling erodible delivery systems, or a combination of these components. These additional components provide compositions which are comfortable and have sustained release.

When administered for the treatment of elevated intraocular pressure of glaucoma, the active compound is most desirably administered topically to the eye, although systemic treatment is also satisfactory.

When given systemically, the drug can be given by any route, although the oral route is preferred. In oral administration the drug can be employed in any of the usual dosage forms such as tablets or capsules, either in a contemporaneous delivery or sustained release form. Any number of the usual excipients or tableting aids can likewise be included.

The active drug of this invention is most suitably administered in the form of ophthalmic pharmaceutical compositions adapted for topical administration to the eye such as a suspension, ointment, or as a solid insert.

The herein before described dosage values are believed accurate for human patients and are based on the known and presently understood pharmacology of the compounds, and the activity of other similar entities in the human eye. As with all medications, dosage requirements are variable and must be individualized on the basis of the disease and the response of the patient.

The pharmaceutical preparation which contains the active compound may be conveniently admixed with a non-toxic pharmaceutical organic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols, antibacterial components such as quaternary ammonium compounds, phenylmercuric salts known to have cold sterilizing properties and which are non-injurious in use, thimerosal, methyl and propyl paraben, benzyl alcohol, buffering ingredients such as sodium chloride, sodium borate, sodium acetate, and other conventional ingredients such as sorbitan monolaurate, polyoxyethylene sorbitan monopalmitylate, dioctyl sodium sulfosuccinate, monothioglycerol, thiosorbitol, ethylenediamine tetraacetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a solid insert.

While many patients find liquid medication to be entirely satisfactory, others may prefer a solid medicament that is topically applied to the eye, for example, a solid dosage form that is suitable for insertion into the cul-de-sac. To this end the carbonic anhydrase inhibiting agent can be included with a non-bioerodable insert, i.e., one which after dispensing the drug remains essentially intact, or a bioerodable insert, i.e., one that either is soluble in lachrymal fluids, or otherwise disintegrates.

For example, one may use a solid water soluble polymer as the carrier for the medicament. The polymer used to form the insert may be any water soluble non-toxic polymer, for example, cellulose derivatives such as methylcellulose, sodium carboxymethyl cellulose, or a hydroxy lower alkyl cellulose such a hydroxyethyl cellulose, hydroxypropyl cellulose, hydroxypropylmethyl cellulose and the like; acrylates such as polyacrylic acid salts, ethyl acrylates, polyacrylamides; natural products such as gelatin, alginates, pectins, tragacanth, karaya, chondrus, agar, acacia; the starch derivatives such as starch acetate, hydroxyethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, and mixtures of said polymers.

The present invention is also directed to methods of treating glaucoma and other ophthalmic diseases and abnormalities. The methods comprise topically applying to the affected eye(s) of the patient a therapeutically effective amount of a composition according to the present invention. The frequency and amount of dosage will be determined by the clinician based on carious clinical factors. The methods will typically comprise topical application of one or two drops (approximately 30 microliters) of a liquid composition, or an equivalent amount of a solid or semi-solid dosage form, to the affected eye one or two times per day.

The present invention is also directed to articles of manufacture which include the active ingredients of the invention in suitable pharmaceutical compositions packaged for distribution in conjunction with labeling or package inserts describing indications and giving dosage instructions. Packaging can be accomplished by any of a number of means utilized in the pharmaceutical industry. Examples of such packaging are: unit dose containers for dispensing liquid compositions enclosed in a box or container along with package inserts; plastic and/or foil wrappers holding solid ocular inserts which contain the active ingredients of the invention and which are enclosed in a box or container along with package inserts. Other modes of packaging would be readily apparent to one skilled in the pharmaceutical packaging arts.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than (be) by the foregoing disclosure.

Having now described the invention, what is claimed is:

1. A method of treating a mammal suffering from glaucoma or ocular hypertension, comprising administering to the mammal a therapeutically effective amount of a prostaglandin and a therapeutically effective amount of an alpha adrenergic agent of formula (I)

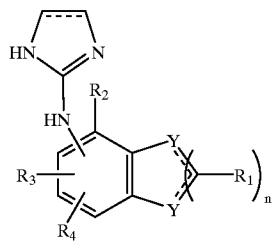

formula (I)

wherein each Y is independently selected from the group consisting of N, N—CH3, O, S and C—$R_1$; $R_1$ is hydrogen, lower alkyl or oxo; $R_2$, $R_3$ and $R_4$ are independently selected from the group consisting of hydrogen, halogen, lower alkyl and lower alkenyl; n is an integer from 1 to 3; and a broken line beside a solid line indicates either a single or a double bond, provided that two double bonds are not on the same carbon in the case when n=1, and their pharmaceutically acceptable salts and esters as appropriate wherein said method provides neuroprotection.

2. The method of claim 1 wherein the prostaglandin is selected from the group consisting of $PGF_{2\alpha}$, $PGE_2$, $PGE_1$, prostacyclin, 15(S)-methyl-$PGF_{2\alpha}$, 16,16-dimethyl-$PGF_{2\alpha}$, 15(S)-methyl-$PGE_2$,16,16-dimethyl-$PGE_2$, 17,18,19,20-tetranor-16-phenoxy-PGE2, 17,18, 19,20-tetranor-16-phenoxy-$PGF_{2\alpha}$, 18,19,20-trinor-17-phenyl-$PGE_2$, 18,19,20-trinor-17-phenyl-$PGF_{2\alpha}$, the free acid and lower alkyl esters of $PGF_{2\alpha}$, wherein the omega chain has been replaced with phenylethylsulfonamidomethyl-, trimoprostil, RS-84–135, rioprostil, S-1033 (15-deshydroxy $PGF_{2\alpha}$, sodium salt), S-747260, nocloprost, CS-412, YPG-209, K-10134, cloprostenol, fluprostenol, luporstiol, etiproston, tiaprost, SQ 27986, ZK 138519, 13,14-dihydro-ZK 138519, ZK 118182, 13,14-dihydro-ZK 118182, ZK 110841, 13,14-dihydro-ZK 110841, PhXA41 (latanoprost), RO-221327, HR-466, HR-601, ONO-1206, UFO-21, 11-deoxy-$PGE_2$, 11-deoxy-$PGF_{2\alpha}$, 11-deoxy-16,16-dimethyl-$PGE_2$, 11-deoxy-15(S)-methyl-$PGE_2$, 11-deoxy-15(S)-methyl-$PGF_{2\alpha}$, misoprostol, enisoprost, MDL-646, CL-115,574, CL-115,347, TR-4161, TR-4752, TR-4367, CP-27987, sulprostone, gemeprost, alfaprostol, delprostenate, prostalene, fenprostalene, CL-116,069, ONO-995 and RO-229648, and their pharmaceutically acceptable esters and salts, as appropriate.

3. The method of claim 2 wherein the prostaglandin is selected from the group consisting of $PGF_{2\alpha}$-11-pivalyl ester, the 1-amido-15-methyl ether of $PGF_{2\alpha}$1-ethylamido-18,19,20-trinor-17-phenyl-$PGF_{2\alpha}$, $PGF_{2\alpha}$-1-ethyl ester, $PGF_{2\alpha}$-1-isopropyl ester, the acid and isopropyl ester derivatives of $PGF_{2\alpha}$ wherein the omega chain has been replaced with phenylethylsulfonamidomethyl-, as represented by the structure below:

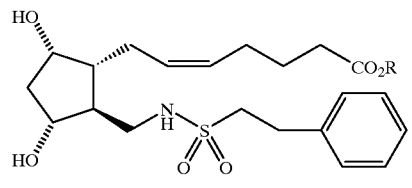

R = H, i-propyl,

RO-229648, SQ 27986, ZK 138519, 13,14-dihydro-ZK 138519, ZK 110841, 13,14-dihydro-ZK 110841, PhXA41, and 18,19,20-trinor-17-phenyl-$PGF_{2\alpha}$-1-methyl ester.

4. The method of claim 1 wherein the alpha adrenergic agent is further selected from formula (I) to contain the groups of formula (II) wherein R2 is bromine or methyl and all other variables are defined as in claim 1.

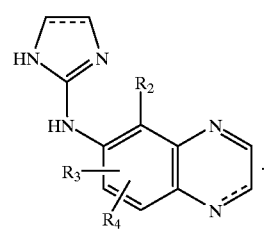

formula (II)

5. The method of claim 3 wherein the alpha adrenergic agent is brimonidine (5-bromo-N-(4,5-dihydro-1H-imidazol-2-yl)-6-quinoxalinamine).

6. The method of claim 4 wherein the alpha adrenergic agent is brimonidine (5-bromo-N-(4,5-dihydro-1H-imidazol-2-yl)-6-quinoxalinamine).

7. The method of claim 1 wherein the prostaglandin is the 11-pivalyl ester of $PGF_{2\alpha}$ and the alpha adrenergic agent is brimonidine.

* * * * *

UNITED STATES PATENT AND TRADEMARK OFFICE
CERTIFICATE OF CORRECTION

PATENT NO. : 6,294,563 B1
DATED : September 25, 2001
INVENTOR(S) : Garst et al.

Page 1 of 1

It is certified that error appears in the above-identified patent and that said Letters Patent is hereby corrected as shown below:

<u>Column 8,</u>
Line 55, delete "$PGF_2)x1$-" and insert in place thereof -- $PGF_{2\alpha}$-1- --
Line 56, delete "38519" and insert in place there -- 138519 --

Signed and Sealed this

Twenty-sixth Day of March, 2002

JAMES E. ROGAN
*Director of the United States Patent and Trademark Office*

*Attest:*

*Attesting Officer*